US00PP19880P2

(12) United States Plant Patent
Klemm

(10) Patent No.: US PP19,880 P2
(45) Date of Patent: Mar. 31, 2009

(54) ***NIEREMBERGIA* PLANT NAMED 'KLENC07344'**

(50) Latin Name: *Nierembergia caerulea*
Varietal Denomination: KLENC07344

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/077,980

(22) Filed: Mar. 24, 2008

(51) Int. Cl.
*A01H 5/00* (2006.01)

(52) U.S. Cl. ..... Plt./459

(58) Field of Classification Search ..... Plt./459
See application file for complete search history.

*Primary Examiner*—Annette H Para
(74) *Attorney, Agent, or Firm*—Jondle & Associates, P.C.

(57) ABSTRACT

A new cultivar of *Nierembergia* particularly characterized by blue flowers, a compact growth habit and very early flowering, is disclosed.

1 Drawing Sheet

Genus and species: *Nierembergia caerulea.*
Variety denomination: 'KLENC07344'.

BACKGROUND OF THE NEW PLANT

The present invention comprises a new and distinct cultivar of *Nierembergia*, botanically known as *Nierembergia caerulea,* and hereinafter referred to by the cultivar name 'KLENC07344'. 'KLENC07344' was discovered as a seedling resulting from a cross conducted between May to September 2004 in Stuttgart, Germany between the proprietary female *Nierembergia* parent, 'X 008' (unpatented) and the proprietary male *Nierembergia* parent, 'X 010' (unpatented). A single plant selection was subsequently chosen for further evaluation and for asexual propagation.

The new cultivar was created in 2004 in Stuttgart, Germany and has been asexually reproduced repeatedly by vegetative cuttings and in-vitro shoot tip culture in Stuttgart, Germany over a three and one-half-year period (more than 30 generations). 'KLENC07344' has been found to retain its distinctive characteristics through successive asexual propagations.

SUMMARY OF THE INVENTION

The following are the most outstanding and distinguishing characteristics of this new cultivar when grown under normal commercial practices in a greenhouse in Stuttgart, Germany.

1. Blue flowers;
2. A compact growth habit; and
3. Very early flowering.

DESCRIPTION OF THE PHOTOGRAPH

This new *Nierembergia* plant is illustrated by the accompanying photograph which shows the whole plant habit of the variety, as well as blooms, buds and foliage; the colors shown are as true as can be reasonably obtained by conventional photographic procedures. The photograph is of a plant about 5-months old and grown from rooted cuttings in a 11-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLENC07344'. The data which define these characteristics were collected from asexual reproductions carried out in Stuttgart, Germany. The plant history was taken on 5-month old plants in 11-cm pots that were pinched once approximately one week after planting and grown in a greenhouse in the spring. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Solanaceae.
- *Genus and species.*—*Nierembergia caerulea.*
- *Common name.*—Nightshade plant, cupflower.

Parentage:
- *Female parent.*—The proprietary *Nierembergia* parent, 'X 008' (unpatented).
- *Male parent.*—The proprietary *Nierembergia* parent, 'X 010' (unpatented).

Plant:
- *Growth habit.*—Compact.
- *Height.*—6.0 cm.
- *Spread.*—19.0 cm.

Branches:
- *Length.*—10.0 cm.
- *Diameter.*—1.0 cm to 3.0 cm.
- *Color.*—RHS 146B.
- *Amount of branching* (*number of lateral branches*).—6.
- *Pubescence.*—Absent.
- *Internode length.*—1.0 cm to 1.5 cm.

Leaves:
- *Arrangement.*—Alternate.
- *Shape.*—Lanceolate.
- *Apex.*—Acute.
- *Base.*—Open.
- *Margin.*—Entire.
- *Length.*—0.5 cm to 1.0 cm.
- *Width.*—0.2 cm.

*Color* (*for both immature and mature leaves*).—Upper surface: RHS 146A. Lower surface: RHS 146B.
*Pubescence.*—Absent.
*Petiole.*—Absent.

Petals:
*Quantity.*—5.
*Shape.*—V-shaped.
*Apex.*—Obtuse.
*Base.*—Broad.
*Margin.*—Entire.
*Color.*—Upper surface: RHS 86B. Lower surface: RHS 86D.
*Corolla.*—Absent.

Reproductive organs:
*Pistil quantity.*—1.
*Stigma color.*—RHS 144A.
*Stamen, quantity.*—Few.
*Type.*—Epigynoecious.
*Anther color.*—RHS 5A.
*Pollen amount.*—Abundant.
*Pollen color.*—RHS 5A.

Fruit and seed set: None observed.

Disease and Insect Resistance: Not observed.

COMPARISON WITH PARENTAL AND COMMERCIAL CULTIVARS

'KLENC07344' differs from the female parent, the proprietary *Nierembergia* 'X 008' (unpatented) in that 'KLENC07344' has a compact growth habit and blue flowers, while 'X 008' has a very compact growth habit and light blue flowers.

'KLENC07344' differs from the male parent, the proprietary *Nierembergia* 'X 010' (unpatented) in that 'KLENC07344' has a compact growth habit and very early flowering, while 'X 010' has a very upright growth habit and late flowering.

'KLENC07344' differs from the commercial comparison variety 'BeBop Blue' (unpatented) in that 'KLENC07344' has a compact growth habit while 'BeBop Blue' has an upright growth habit. Additionally, 'KLENC07344' has earlier flowering than 'BeBop Blue'.

I claim:

1. A new and distinct cultivar of *Nierembergia* plant as shown and described herein.

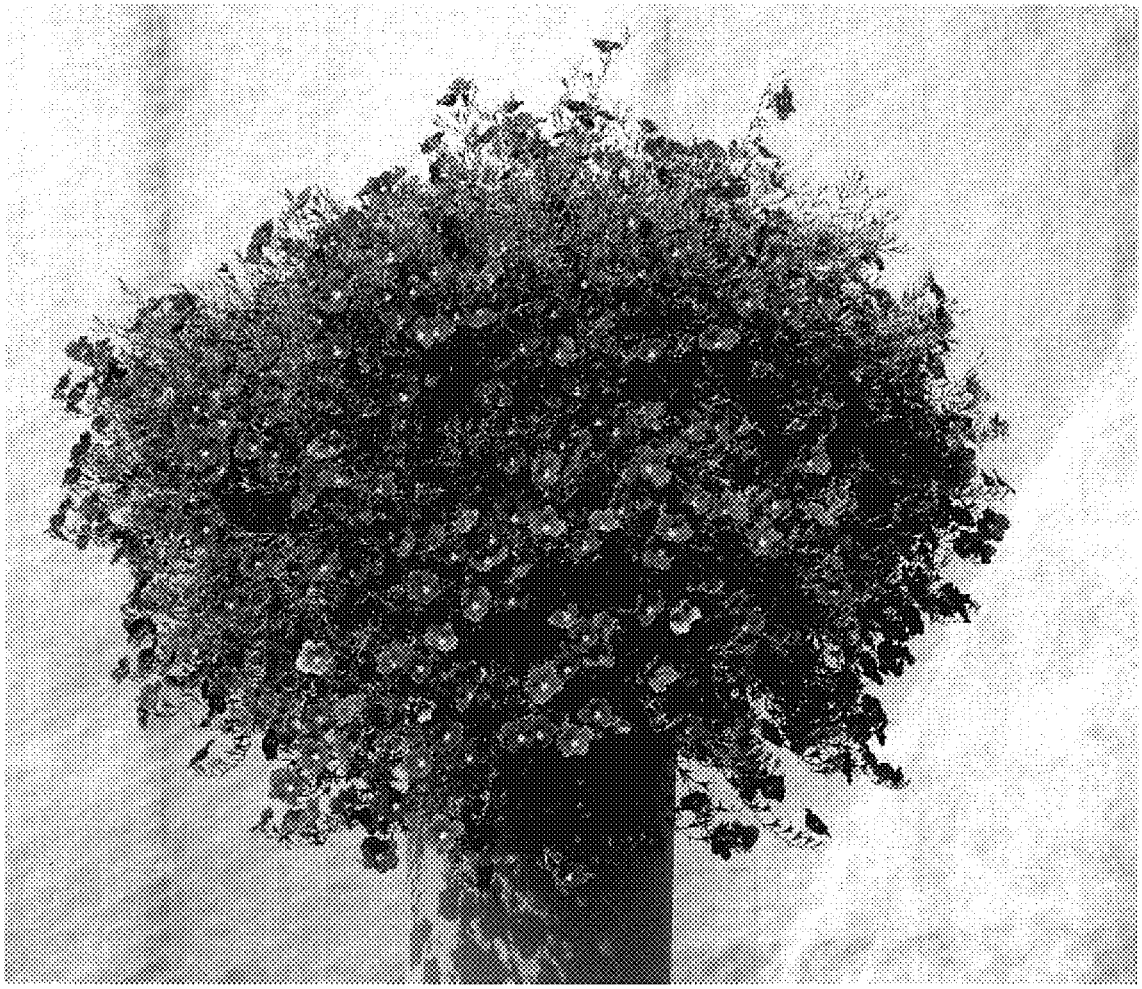

* * * * *